(12) United States Patent
Chen et al.

(10) Patent No.: US 8,609,711 B2
(45) Date of Patent: Dec. 17, 2013

(54) CRYSTALLINE N-{(1S)-2-AMINO-1-[(3-FLUOROPHENYL)METHYL]ETHYL}-5-CHLORO-4-(4-CHLORO-1-METHYL-1H-PYRAZOL-5-YL)-2-THIOPHENECARBOXAMIC HYDROCHLORIDE

(75) Inventors: Pingyun Y. Chen, Durham, NC (US); Jeffrey Gaulding, Tucker, GA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 577 days.

(21) Appl. No.: 12/695,331

(22) Filed: Jan. 28, 2010

(65) Prior Publication Data

US 2010/0197754 A1    Aug. 5, 2010

Related U.S. Application Data

(60) Provisional application No. 61/148,490, filed on Jan. 30, 2009.

(51) Int. Cl.
*A61K 31/415* (2006.01)
*C07D 231/16* (2006.01)

(52) U.S. Cl.
USPC ........................................ 514/406; 548/365.7

(58) Field of Classification Search
USPC ........................................ 514/406; 548/365.7
See application file for complete search history.

(56) References Cited

U.S. PATENT DOCUMENTS

| | | | |
|---|---|---|---|
| 4,987,132 A | 1/1991 | Mase et al. | |
| 4,999,359 A | 3/1991 | Vecchietti et al. | |
| 5,201,934 A | 4/1993 | Muenster et al. | |
| 5,258,357 A | 11/1993 | Muenster et al. | |
| 5,369,124 A | 11/1994 | Elbe et al. | |
| 5,595,872 A | 1/1997 | Wetterau, II et al. | |
| 5,631,269 A | 5/1997 | Broughton et al. | |
| 5,668,148 A | 9/1997 | Payne et al. | |
| 5,786,373 A | 7/1998 | Hartman et al. | |
| 5,958,950 A | 9/1999 | Padia et al. | |
| 5,972,980 A | 10/1999 | Cornicelli et al. | |
| 5,998,336 A | 12/1999 | Holcomb | |
| 6,001,866 A | 12/1999 | Cornicelli et al. | |
| 6,130,333 A | 10/2000 | Huang et al. | |
| 6,162,819 A | 12/2000 | Schindler et al. | |
| 6,174,887 B1 | 1/2001 | Haruta et al. | |
| 6,192,967 B1 | 2/2001 | Huang | |
| 6,211,367 B1 | 4/2001 | Cavalla et al. | |
| 6,420,561 B1 | 7/2002 | Haruta et al. | |
| 6,469,171 B1 | 10/2002 | Banwell et al. | |

(Continued)

FOREIGN PATENT DOCUMENTS

| | | |
|---|---|---|
| CA | 2361636 A1 | 8/2000 |
| CN | 1733708 | 2/2006 |

(Continued)

OTHER PUBLICATIONS

Vippagunta et al. (Advanced Drug Delivery Reviews, 48 (2001) 3-26).*

(Continued)

*Primary Examiner* — Noble Jarrell
*Assistant Examiner* — Valerie Rodriguez-Garcia
(74) *Attorney, Agent, or Firm* — Wayne J. Dustman; Edward R. Gimmi (57) ABSTRACT

An improved AKT inhibiting compound, crystalline N-{(1S)-2-amino-1-[(3-fluorophenyl)methyl]ethyl}-5-chloro-4-(4-chloro-1-methyl-1H-pyrazol-5-yl)-2-thiophenecarboxamide hydrochloride.

11 Claims, 3 Drawing Sheets

(56) References Cited

U.S. PATENT DOCUMENTS

| | | |
|---|---|---|
| 6,545,055 B1 | 4/2003 | Zhu et al. |
| 6,624,309 B1 | 9/2003 | Lloyd et al. |
| 6,638,980 B1 | 10/2003 | Su et al. |
| 6,649,638 B1 | 11/2003 | Brown et al. |
| 6,750,239 B2 | 6/2004 | Hale et al. |
| 6,770,666 B2 | 8/2004 | Hashimoto et al. |
| 6,875,789 B2 | 4/2005 | Tang et al. |
| 6,897,208 B2 | 5/2005 | Edwards et al. |
| 6,914,069 B2 | 7/2005 | Shroff et al. |
| 6,982,279 B2 | 1/2006 | Peukert et al. |
| 7,034,049 B1 | 4/2006 | Pevarello et al. |
| RE39,088 E | 5/2006 | Haruta et al. |
| 7,041,687 B2 | 5/2006 | Binch et al. |
| 7,074,801 B1 | 7/2006 | Yoshida et al. |
| 7,112,600 B1 | 9/2006 | Hashimoto et al. |
| 7,125,883 B1 | 10/2006 | Zechel et al. |
| 7,157,456 B2 | 1/2007 | Straub et al. |
| 7,166,619 B2 | 1/2007 | Li et al. |
| 7,223,788 B2 | 5/2007 | Schwink et al. |
| 7,285,554 B2 | 10/2007 | Kubota et al. |
| 7,314,885 B2 | 1/2008 | Aronov et al. |
| 7,335,779 B2 | 2/2008 | Ammendola et al. |
| 7,521,473 B2 | 4/2009 | Lee et al. |
| 2002/0002183 A1 | 1/2002 | Zhu et al. |
| 2002/0103202 A1 | 8/2002 | Pinto et al. |
| 2002/0132844 A1 | 9/2002 | Shroff et al. |
| 2003/0105143 A1 | 6/2003 | Ammendola et al. |
| 2003/0139452 A1 | 7/2003 | Tang et al. |
| 2003/0144276 A1 | 7/2003 | Kikuchi et al. |
| 2003/0144337 A1 | 7/2003 | Hale et al. |
| 2003/0158238 A1 | 8/2003 | Hale et al. |
| 2003/0195240 A1 | 10/2003 | Kalindjian et al. |
| 2003/0220365 A1 | 11/2003 | Stewart et al. |
| 2004/0014774 A1 | 1/2004 | Myers et al. |
| 2004/0014971 A1 | 1/2004 | Meerpoel et al. |
| 2004/0034037 A1 | 2/2004 | Harbeson et al. |
| 2004/0063671 A1 | 4/2004 | Arrhenius et al. |
| 2004/0077707 A1 | 4/2004 | Desai et al. |
| 2004/0116399 A1 | 6/2004 | Zhu et al. |
| 2004/0116425 A1 | 6/2004 | Li et al. |
| 2004/0132726 A1 | 7/2004 | Arora et al. |
| 2004/0198799 A1 | 10/2004 | Brondyk et al. |
| 2005/0026985 A1 | 2/2005 | Shroff et al. |
| 2005/0032848 A1 | 2/2005 | Aquino et al. |
| 2005/0107436 A1 | 5/2005 | Xie et al. |
| 2005/0130954 A1 | 6/2005 | Mitchell et al. |
| 2005/0148605 A1 | 7/2005 | Grotzfeld et al. |
| 2005/0153978 A1 | 7/2005 | Alberti et al. |
| 2005/0154202 A1 | 7/2005 | Hagmann et al. |
| 2005/0182075 A1 | 8/2005 | Yuan |
| 2005/0197328 A1 | 9/2005 | Bailey et al. |
| 2006/0014816 A1 | 1/2006 | Arnold et al. |
| 2006/0052384 A1 | 3/2006 | Bouillot et al. |
| 2006/0058351 A1 | 3/2006 | Diaz et al. |
| 2006/0074119 A1 | 4/2006 | Andrews et al. |
| 2006/0128690 A1 | 6/2006 | Ishihara et al. |
| 2006/0135773 A1 | 6/2006 | Semple et al. |
| 2006/0148862 A1 | 7/2006 | Clary et al. |
| 2006/0247260 A1 | 11/2006 | Murata et al. |
| 2006/0252807 A1 | 11/2006 | Severance et al. |
| 2006/0288588 A1 | 12/2006 | Morabito |
| 2006/0293320 A1 | 12/2006 | Schmitz et al. |
| 2007/0004771 A1 | 1/2007 | Lee et al. |
| 2007/0021713 A1 | 1/2007 | Kumar et al. |
| 2007/0123561 A1 | 5/2007 | Lee et al. |
| 2007/0149549 A1 | 6/2007 | Li et al. |
| 2007/0149561 A1 | 6/2007 | Dhanak et al. |
| 2007/0173521 A1 | 7/2007 | Xue et al. |
| 2007/0203154 A1 | 8/2007 | Zhou et al. |
| 2007/0265271 A1 | 11/2007 | Peters et al. |
| 2008/0009506 A1 | 1/2008 | Kusama et al. |
| 2008/0027044 A1 | 1/2008 | Lewis et al. |
| 2008/0090882 A1 | 4/2008 | Dorsch et al. |
| 2008/0119456 A1 | 5/2008 | Ulven et al. |
| 2008/0171741 A1 | 7/2008 | Wrobleski et al. |
| 2008/0188528 A1 | 8/2008 | Biediger et al. |
| 2009/0136979 A1 | 5/2009 | Jones et al. |
| 2009/0181983 A1 | 7/2009 | Corte |
| 2009/0186905 A1 | 7/2009 | Leahy et al. |
| 2010/0197754 A1 | 8/2010 | Chen et al. |

FOREIGN PATENT DOCUMENTS

| | | |
|---|---|---|
| DE | 3927483 A1 | 8/1989 |
| DE | 19904396 | 2/1999 |
| DE | 102004051277 | 10/2004 |
| DE | 102004054666 | 5/2006 |
| EP | 0335381 | 3/1989 |
| EP | 0712397 | 4/1999 |
| EP | 1498109 A1 | 2/2004 |
| EP | 1802583 A1 | 10/2004 |
| ES | 2005163 | 3/1989 |
| JP | 2000/256358 | 9/2000 |
| JP | 2001/247569 | 9/2001 |
| JP | 2005336172 | 12/2005 |
| JP | 2006232707 | 9/2006 |
| JP | 2007277230 A | 10/2007 |
| WO | WO9315047 | 8/1993 |
| WO | WO 94/29300 | 12/1994 |
| WO | WO9736585 | 10/1997 |
| WO | WO9736875 | 10/1997 |
| WO | WO9736881 | 10/1997 |
| WO | WO9736886 | 10/1997 |
| WO | WO9736890 | 10/1997 |
| WO | WO9736896 | 10/1997 |
| WO | WO9736897 | 10/1997 |
| WO | WO9736898 | 10/1997 |
| WO | WO9736901 | 10/1997 |
| WO | WO00035919 | 6/2000 |
| WO | WO0138309 | 3/2001 |
| WO | WO0156557 | 8/2001 |
| WO | WO0156993 | 8/2001 |
| WO | WO0157022 | 8/2001 |
| WO | WO 02/07823 A2 | 1/2002 |
| WO | WO 03/011855 A2 | 2/2003 |
| WO | WO 2003035619 | 5/2003 |
| WO | WO 2005/019182 | 3/2005 |
| WO | WO2005019200 | 3/2005 |
| WO | WO 2005/077345 | 8/2005 |
| WO | WO2005074642 | 8/2005 |
| WO | WO2005077373 | 8/2005 |
| WO | WO2005095386 | 10/2005 |
| WO | WO2006084176 | 8/2006 |
| WO | WO2006110762 | 10/2006 |
| WO | WO 2006/136823 A1 | 12/2006 |
| WO | WO 2006/136837 | 12/2006 |
| WO | WO2006129199 | 12/2006 |
| WO | WO2006136829 | 12/2006 |
| WO | WO2007002559 | 1/2007 |
| WO | WO2007002563 | 1/2007 |
| WO | WO2007052843 | 5/2007 |
| WO | WO2007/076423 A2 | 7/2007 |
| WO | WO 2007/087906 | 8/2007 |
| WO | WO2008080056 | 7/2008 |
| WO | WO 2008/098104 * | 8/2008 |
| WO | WO2008/098105 A1 | 8/2008 |
| WO | WO2008098105 | 8/2008 |
| WO | WO2008121685 | 10/2008 |
| WO | WO2008121786 | 10/2008 |

OTHER PUBLICATIONS

Altomare, et al., *Oncogene*, 24(40):6080-6089 (2005).

Clinical Trials.gov, *Repeat Dose Safety Study for Compond to Treat Hematologic Cancer*, Study 1 of 1 for search of: GSK2110183, First Received on Mar. 20, 2009 (pp. 1-5).

Clinical Trials.gov, *A Study of MK2206 in Locally Advanced or Metastatic Solid Tumors* (2206-007), Study 2 of 35 for search of:MK2206, First Received on Feb. 17, 2010 (pp. 1-4).

Clinical Trials.gov, *MK-2206 in the Treatment of Recurrent Platinum-Resistant Ovarian, Fallopian Tube, or Peritoneal Cancer*, Study 7 of 35 for search of:MK2206, First Received on Jan. 24, 2011 (pp. 1-4).

(56) References Cited

OTHER PUBLICATIONS

Clinical Trials.gov, *MK2206 in Treating Patients With Advanced Gastric or Gastroesophageal Junction Cancer*, Study 11 of 35 for search of:MK2206, First Received on Dec. 14, 2010 (pp. 1-5).
Clinical Trials.gov, *MK2206 in Treating Patients with Stage I, Stage II, or Stage III Breast Cancer*, Study 12 of 35 for search of:MK2206, First Received on Mar. 18, 2011 (pp. 1-5).
Clinical Trials.gov, *Study of MK-2206 in Patients With Metastatic Neuroendocrine Tumors (NET)*, Study 14 of 35 for search of:MK2206, First Received on Jul. 21, 2010 (pp. 1-5).
Clinical Trials.gov, *Bicalutamide With or Without MK2206 in Treating Patients with Previously Treated Prostate Cancer*, Study 15 of 35 for search of:MK2206, First Received on Dec. 1, 2010 (pp. 1-6).
Clinical Trials.gov, *MK-2206 for Recurrent Malignant Glioma*, Study 16 of 35 for search of:MK2206, First Received on Nov. 24, 2010 (pp. 1-6).
Clinical Trials.gov, *Akt Inhibitor MK-2206 in Patients W/Advanced Breast Cancer Who Have Tumors With a P1K3CA Mutation and/or PTEN Loss*, Study 17 of 35, search of:MK2206, First Rec'd on Jan 13, 2011 (pp. 1-5).
Clinical Trials.gov, *AKT Kinase Inhibitor MK-2206 With Relapsed Refractory Acute Myelogenous Leukemia*, Study 18 of 35 for search of:MK2206, First Received on Dec. 1, 2010 (pp. 1-4).
Clinical Trials.gov, *Clinical and Translational Study of MK-2206 In Patients With Metastatic KRAS-Wild-Type, P1K3CA-Mutated, Colorectal Cancer*, Study 19 of 35,search of:MK2206, First Rec'd on Aug. 20, 2010 (pp. 1-5).
Clinical Trials.gov, *Study of MK-2206 in Patients With Relapsed Lymphoma*, Study 21 of 35 for search of:MK2206, First Received on Dec. 10, 2010 (pp. 1-4).
Clinical Trials.gov, *MK2206 in Treating Younger Patients With Recurrent or Refractory Solid Tumors or Leukemia*, Study 23 of 35 for search of:MK2206, First Received on Oct. 29, 2010 (pp. 1-8).
Clinical Trials.gov, *MK2206 in Treating Patients With Recurrent or Metastatic Head and Neck Cancer*, Study 25 of 35 for search of:MK2206, First Received on May 6, 2011 (pp. 1-5).
Clinical Trials.gov, *MK2206 in Treating Patients with Recurrent or Advanced Endometrial Cancer*, Study 28 of 35 for search of:MK2206, First Received on Mar. 1, 2011 (pp. 1-6).
Clinical Trials.gov, *MK2206 or Everolimus in Treating Patients With Refractory Kidney Cancer*, Study 30 of 35 for search of:MK2206, First Received on Nov. 10, 2010 (pp. 1-6).
Clinical Trials.gov, *MK2206 in Treating Patients With Advanced Liver Cancer That Did Not Respond to Previous Therapy*, Study 33 of 35 for search of:MK2206, First Received on Nov. 10, 2010 (pp. 1-7).
Clinical Trials.gov, *Molecular Profiling and Targeted Therapy for Advanced Non-Small Cell Lung Cancer, Small Cell Lung Cancer and Thymic Malignancies*, Study 35 of 35 for search of:MK2206, First Received on Feb. 26, 2011 (pp. 1-10).
EP Supplementary Search Report, Apr. 27, 2011, Ref. RCS/PU62316, PCT/US2008053269, 27.04.11.
Hernando, et al., *Nature Medicine*, 13(6):748-753 (2007).
Hideshima, et al., *Blood*, 107:4053-4062 (2006).
Ringel, et al., *Cancer Research*, 61(16):6105-6111 (2001).
Steelman, et al., *Expert Opinion on Therapeutic Targets*, 12(9):1139-1165 (2008).
Yonetoku, et al., *Bioorganic & Medicinal Chemistry*, 14(14):4750-4760 (2006).
Adams, et al., *Science*, 281:1322-1326 (1998).
Alessi, et al., *EMBO J.*, 15:6541-6551 (1996).
Backman, S., et al., *Current Opinion in Neurobiology*, 12(5):516 (2002).
Bartroli, et al., *J. Med. Chem.*, 1998, vol. 41, No. 11, pp. 1855-1868.
Bellacosa, et al., *Int. J. Cancer*, 64:280-285 (1995).
J.C. Byrd, S. Stilgenbauer and I. W. Flinn, "Chronic lymphocytic leukemia." *Hematology/the Education Program of the American Society of Hematology*. American Society of Hematology. Education Program, 163-83 (2004).

Cheng, et al., *Proc. Natl. Acad. Sci. U.S.A.*, 89:9267-9271 (1992).
Cheng, et al., *Proc. Natl. Acad. Sci. U.S.A.*, 93:3636-3641 (1996).
ClinicalTrials.gov, Study 2 of 2 for search of: GSK2110183, Mar. 20, 2009, "Repeat Dose Safety Study for Compound to Treat Hematologic Cancer".
Dalvit, et al., *J. Am. Chem. Soc.*, 2003, vol. 125, No. 25, pp. 7696-7703.
Downward, *Curr. Opin. Cell. Biol.*, 10:262-267 (1998).
Downward, *Science*, 279:673-674 (1998).
Dudek, et al., *Science*, 275:661-665 (1997).
Einzig et. al., *Proc. Am. Soc. Clin. Oncol.*, 20:46 (2001).
Forastire et. al., *Sem. Oncol.*, 20:56 (1990).
Franke, et al., *Cell*, 81:727-736 (1995).
Franke, et al., *Cell*, 88:435-437 (1997).
Hemmings, *Science*, 275:628-630 (1997).
Hemmings, *Science*, 277:534 (1997).
Holmes et al., *J. Nat. Cancer Inst.*, 83:1797 (1991).
Kauffmann-Zeh, et al., *Nature*, 385:544-548 (1997).
Kearns, C.M. et. al., *Seminars in Oncology*, 3(6) p. 16-23 (1995).
Kingston et al., *Studies in Organic Chemistry*, 26: 219-235 (1986).
Komander et al., *Biochem. J.*, 375(2):255-262 (2003).
Kulik, et al., *Mol. Cell. Biol.*, 17:1595-1606 (1997).
Kumar, *J. Biol. Chem.*, 256: 10435-10441 (1981).
Li, et al., Guldberg, et al., *Cancer Research*, 57:3660-3663 (1997).
Liaw, et al., *Nature Genetics*, 16:64-67 (1997).
Lin, et al., *Bioorganic and Medicinal Chemistry Letters*, 16(16): 4163-4168; 4163; 4166-4167 (2006).
Liu, et al., *Current Opinion Pharmacology*, 3:317-22 (2003).
Lu, et al., *J. Med. Chem.*, 2006, vol. 49, No. 17, pp. 5154-5161.
Maehama, T., et al., *Annual Review of Biochemistry*, 70:247 (2001).
Markman et al., *Yale Journal of Biology and Medicine*, 64:583-590 (1991).
McGuire et al., *Ann. Intern., Med.*, 111:273 (1989).
Meier, et al., *J. Biol. Chem.*, 272:30491-30497 (1997).
Nakatani, et al., *J. Biol. Chem.*, 274:21528-21532 (1999).
Parsons, R.; Simpson, L., *Methods in Molecular Biology*, 222:147 (2003).
Risinger, et al., *Cancer Research*, 57:4736-4738 (1997).
Salvino, et al. *J. Comb. Chem.*, 2000, vol. 2, pp. 691-697.
Staal, *Proc. Natl. Acad. Sci. U.S.A.*, 84:5034-7 (1987).
Schiff et al., *Nature*, 277:665-667 (1979).
Schiff et al., *Proc. Natl. Acad. Sci. USA*, 77:1561-1565 (1980).
Seefeld, et al., *Bioorganic & Medicinal Chem. Ltrs.*, 19:2244-2248 (2009).
Stal, et al., *Breast Cancer Research*, 5:R37-R44 (2003).
Stambolic, et al., *Cell*, 95:29-39 (1998).
Sun, et al., *Proc. Natl. Acad. Sci. U.S.A.*, 96:6199-6204 (1999).
Sun, et al., *Am. J. Pathol.*, 159:431-7 (2001).
Mitsunobu, *Synthesis*, 1-28 (1981).
Thornberry, et al., *Science*, 281:1312-1316 (1998).
Wani et al., *J. Am. Chem. Soc.*, 93:2325 (1971).
Williams, et al., *Curr. Biol.*, 10:439-448 (2000).
Woo et. al., *Nature*, 368:750 (1994).
Yonetoku, et al. Bioorganic & Med. Chem, 2006, vol. 14, No. 15, pp. 5370-5383.
Written Opinion of the International Searching Authority and International Search Report for PCT/US2010/022323, Opinion dated Apr. 9, 2010.
Bavin, et al., *Chemistry & Industry*, 21:527-529 (1989).
Bryn, et al., *Pharmaceutical Research*, 12(7):945-954 (1995).
Caira, *Topics in Current Chemistry*, 198:163-208 (1998).
Hancock, et al., *Journal of Pharmaceutical Sciences*, 86(1):1-12 (1997).
Ahlneck, et al., *International Journal of Pharmaceutics*, 62(2-3):87-95 (1990).

* cited by examiner

CRYSTALLINE N-{(1S)-2-AMINO-1-[(3-FLUOROPHENYL)METHYL]ETHYL}-5-CHLORO-4-(4-CHLORO-1-METHYL-1H-PYRAZOL-5-YL)-2-THIOPHENECARBOXAMIC HYDROCHLORIDE

CROSS REFERENCE TO PRIOR APPLICATIONS

This application claims the benefit of U.S. Provisional Application No. 61/148,490 filed Jan. 30, 2009.

FIELD OF THE INVENTION

This invention relates to an improved protein kinase B (hereinafter PKB/Akt, PKB or AKT) inhibiting compound, the hydrochloride salt of N-{(1S)-2-amino-1-[(3-fluorophenyl)methyl]ethyl}-5-chloro-4-(4-chloro-1-methyl-1H-pyrazol-5-yl)-2-thiophenecarboxamide in crystalline form. The compound is represented by Structure I:

(I)

The compound of this invention is useful as an inhibitor of AKT activity, and in the treatment of cancer and arthritis.

DETAILED DESCRIPTION OF THE INVENTION

N-{(1S)-2-Amino-1-[(3-fluorophenyl)methyl]ethyl}-5-chloro-4-(4-chloro-1-methyl-1H-pyrazol-5-yl)-2-thiophenecarboxamide is a compound which is disclosed and claimed, along with pharmaceutically acceptable salts thereof, as being useful as an inhibitor of AKT activity, particularly in the treatment of cancer and arthritis, in International Application No. PCT/US08/053269, having an International filing date of Feb. 7, 2008; International Publication Number WO 08/098104 and an International Publication date of Aug. 14, 2008 (compound of Example 96). The entire disclosure of which is hereby incorporated by reference. International Application No. PCT/US08/053269 discloses the preparation of N-{(1S)-2-amino-1-[(3-fluorophenyl)methyl]ethyl}-5-chloro-4-(4-chloro-1-methyl-1H-pyrazol-5-yl)-2-thiophenecarboxamide hydrochloride. However the hydrochloride form prepared by the process in Example 96 of International Application No. PCT/US08/053269 is amorphous.

It has now been found that the hydrochloride salt of N-{(1S)-2-amino-1-[(3-fluorophenyl)methyl]ethyl}-5-chloro-4-(4-chloro-1-methyl-1H-pyrazol-5-yl)-2-thiophenecarboxamide can be prepared in crystalline form and that the crystalline form has numerous advantages over the free acid and other salt forms, including the amorphous hydrochloride form. The crystalline form of N-{(1S)-2-amino-1-[(3-fluorophenyl)methyl]ethyl}-5-chloro-4-(4-chloro-1-methyl-1H-pyrazol-5-yl)-2-thiophenecarboxamide hydrochloride is more readily formulated into pharmaceutical dosage forms, particularly tablets and has improved chemical stability. The crystalline form is a non-hygroscopic anhydrous form, and exhibits good solubility in bio-relevant media. The amorphous form is hygroscopic.

While the free compound is highly useful as an inhibitor of AKT activity, particularly in treating cancer and arthritis, the crystalline form of the hydrochloride salt of N-{(1S)-2-amino-1-[(3-fluorophenyl)methyl]ethyl}-5-chloro-4-(4-chloro-1-methyl-1H-pyrazol-5-yl)-2-thiophenecarboxamide has added advantages.

The compound of this invention, N-{(1S)-2-amino-1-[(3-fluorophenyl)methyl]ethyl}-5-chloro-4-(4-chloro-1-methyl-1H-pyrazol-5-yl)-2-thiophenecarboxamide hydrochloride in crystalline form (hereinafter—"Active Ingredient" or "Compound A"), is useful as an inhibitor of AKT activity, particularly in the treatment of cancer and arthritis. The Active Ingredient can be administered in a conventional dosage form prepared by combining the Active Ingredient with a conventional pharmaceutically acceptable carrier or diluent according to techniques readily known to those of skill in the art, such as those described in International Application No. PCT/US08/053269.

Suitably, the present invention includes within its scope pharmaceutical compositions comprising N-{(1S)-2-amino-1-[(3-fluorophenyl)methyl]ethyl}-5-chloro-4-(4-chloro-1-methyl-1H-pyrazol-5-yl)-2-thiophenecarboxamide hydrochloride in crystalline form, as the Active Ingredient, in association with a pharmaceutically acceptable carrier or diluent. Compound A of this invention can be administered by oral, parenteral, intradermal or topical routes of administration. The term parenteral as used herein includes intravenous, intramuscular, subcutaneous, intranasal, intrarectal, intravaginal and intraperitoneal administration. Oral administration is generally preferred. Compound A can be formulated in dosage forms appropriate for each route of administration including capsules, tablets, pills, powders and granules. In such solid dosage forms, the active compound is generally admixed with at least one inert diluent. The oral dosage forms can also comprise, as is normal practice, additional substances other than inert diluents, e.g., lubricating agents, glidants and antioxidants. In the case of capsules, tablets and pills, the dosage forms may also comprise buffering agents. Tablets and pills can additionally be prepared for a sustained release.

Preparations according to this invention for parenteral administration include sterile aqueous solutions although nonaqueous suspensions of emulsions can be employed. Such dosage forms may also contain adjuvants such as preserving, wetting, osmotic, buffering, emulsifying and dispersing agents. They may be sterilized by, for example, filtration through a bacteria retaining filter, by incorporating sterilizing agents into the compositions, irradiating the compositions or by heating the compositions.

Doses of the presently invented Active Ingredient in a pharmaceutical dosage unit as described above will be an efficacious quantity preferably selected from the range of 0.001-100 mg/kg of total body weight, preferably 0.001-50 mg/kg. When treating a human patient in need of AKT inhibition, in need of treatment for cancer, in need of treatment for arthritis, the selected dose is preferably administered from 1-6 times daily, orally or parenterally. Preferred forms of parenteral administration include topically, rectally, transdermally, by injection and continuously by infusion. Oral dosage units for human administration preferably contain from 0.05 to 3500 mg of Active Ingredient, most preferably from 0.5 to 1,000 mg of Active Ingredient. Oral administration, which uses lower dosages is preferred. Parenteral administration, at high dosages, however, also can be used when safe and convenient for the patient. The above dosages relate to the preferred amount of the Active Ingredient expressed as the free acid.

It will be recognized by one of skill in the art that the optimal quantity and spacing of individual dosages of the Active Ingredient will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of the Active Ingredient given per day for a defined number of days, can be ascertained by those skilled in the art using conventional course of treatment determination tests.

Generally speaking, the compound of this invention is prepared by dissolving the free base, N-{(1S)-2-amino-1-[(3-fluorophenyl)methyl]ethyl}-5-chloro-4-(4-chloro-1-methyl-1H-pyrazol-5-yl)-2-thiophenecarboxamide, in an appropriate organic solvent, such as methyl t-butyl ether (MTBE), then adding to this solution HCl, for example, 4M HCl in dioxane, with heating, for example to 42° C. for 4 hours. The solution is allowed to cool and the compound of this invention is filtered off and dried, for example, dried in vacuo or air dried at an elevated temperature.

Organic solvents are available from the Aldrich Chemical Company, Milwaukee, Wis.

Because the pharmaceutically active compound of the present invention is active as an inhibitor or AKT it exhibits therapeutic utility in treating cancer and arthritis.

Suitably, the present invention relates to a method for treating or lessening the severity of a cancer selected from: brain (gliomas), glioblastomas, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, ovarian, pancreatic, prostate, sarcoma, osteosarcoma, giant cell tumor of bone, thyroid, Lymphoblastic T cell leukemia, Chronic myelogenous leukemia, Chronic lymphocytic leukemia, Hairy-cell leukemia, acute lymphoblastic leukemia, acute myelogenous leukemia, Chronic neutrophilic leukemia, Acute lymphoblastic T cell leukemia, Plasmacytoma, Immunoblastic large cell leukemia, Mantle cell leukemia, Multiple myeloma Megakaryoblastic leukemia, multiple myeloma, acute megakaryocytic leukemia, promyelocytic leukemia, Erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, lung cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

As disclosed in PCT/US2008/053269, the compound of this invention prepared as in PCT/US2008/053269 was tested for activity generally according to the AKT enzyme assays disclosed in PCT/US2008/053269, and in at least one experimental run exhibited a pIC50 value: equal to 9.0 against full length AKT1; equal to 8.0 against full length AKT2; and equal to 8.8 against full length AKT3.

By the term "treating" and derivatives thereof as used herein, is meant therapeutic therapy. Prophylactic therapy is appropriate, for example, when a subject is considered at high risk for developing cancer, or when a subject has been exposed to a carcinogen.

As used herein, the term "effective amount" and derivatives thereof means that amount of a drug or pharmaceutical agent that will elicit the biological or medical response of a tissue, system, animal or human that is being sought, for instance, by a researcher or clinician. Furthermore, the term "therapeutically effective amount" and derivatives thereof means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

By the term "co-administering" and derivatives thereof as used herein is meant either simultaneous administration or any manner of separate sequential administration of Compound A and a further active ingredient or ingredients, known to be useful in the treatment of cancer, including chemotherapy and radiation treatment, or to be useful in the treatment of arthritis. The term further active ingredient or ingredients, as used herein, includes any compound or therapeutic agent known to or that demonstrates advantageous properties when administered to a patient in need of treatment for cancer or arthritis. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of cancer in the present invention. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Examples of a further active ingredient or ingredients (antineoplastic agent) for use in combination or co-administered with the presently invented Compound A are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2$/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem., Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intern, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine, N-tert-butyl ester, 13-ester with 5β-20-epoxy-1,2α, 4,7β, 10β,13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine [1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-O—(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-O—(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2(1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl)methyl] methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I: DNA: irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of formula A following, currently under development, including the racemic mixture (R,S) form as well as the R and S enantiomers:

A known by the chemical name "7-(4-methylpiperazino-methylene)-10,11-ethylenedioxy-20(R,S)-camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; 5,491, 237 and pending U.S. Pat. No. 8,977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/ or follicle stimulating hormone (FSH) for the treatment prostatic carcinoma, for instance, LHRH agonists and antagagonists such as goserelin acetate and luprolide.

Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3 domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases for use in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Inhibitors of Phosphotidyl inositol-3 Kinase family members including blockers of PI3-kinase, ATM, DNA-PK, and Ku may also be useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also of interest in the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kinases, Breast Cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Non-receptor kinase angiogenesis inhibitors may also be useful in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Accordingly, non-receptor tyrosine kinase inhibitors may be used in combination with the compounds of the present invention. For example, anti-VEGF antibodies, which do not recognize VEGFR (the receptor tyrosine kinase), but bind to the ligand; small molecule inhibitors of integrin (alpha$_v$ beta$_3$) that will inhibit angiogenesis; endostatin and angiostatin (non-RTK) may also prove useful in combination with the disclosed compounds. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Agents used in immunotherapeutic regimens may also be useful in the present invention. There are a number of immunologic strategies to generate an immune response. These strategies are generally in the realm of tumor vaccinations. The efficacy of immunologic approaches may be greatly enhanced through combined inhibition of signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. patents (2000) 10(2):215-230.

In one embodiment, the cancer treatment method of the claimed invention includes the co-administration of Compound A and at least one anti-neoplastic agent, such as one selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, and cell cycle signaling inhibitors.

Compound A of this invention is useful as an inhibitor of AKT, in the treatment of cancer and arthritis in mammals, particularly humans, in need thereof.

The method of this invention of treating cancer and arthritis in mammals, including humans, comprises administering to a subject in need of such treatment a therapeutically effective amount of Compound A of the present invention.

The invention also provides for the use of Compound A in the manufacture of a medicament for use in therapy.

The invention also provides for the use of Compound A in the manufacture of a medicament for use as an AKT inhibitor.

The invention also provides for the use of Compound A in the manufacture of a medicament for use in treating cancer.

The invention also provides for the use of Compound A in the manufacture of a medicament for use in treating arthritis.

The invention also provides for a pharmaceutical composition for use in the treatment of cancer which comprises Compound A and a pharmaceutically acceptable carrier.

The invention also provides for a pharmaceutical composition for use in the treatment of arthritis which comprises Compound A and a pharmaceutically acceptable carrier.

The following examples further illustrate the present invention. The examples are not intended to limit the scope of the invention as defined hereinabove and as claimed below.

EXAMPLE 1

Figure 1:
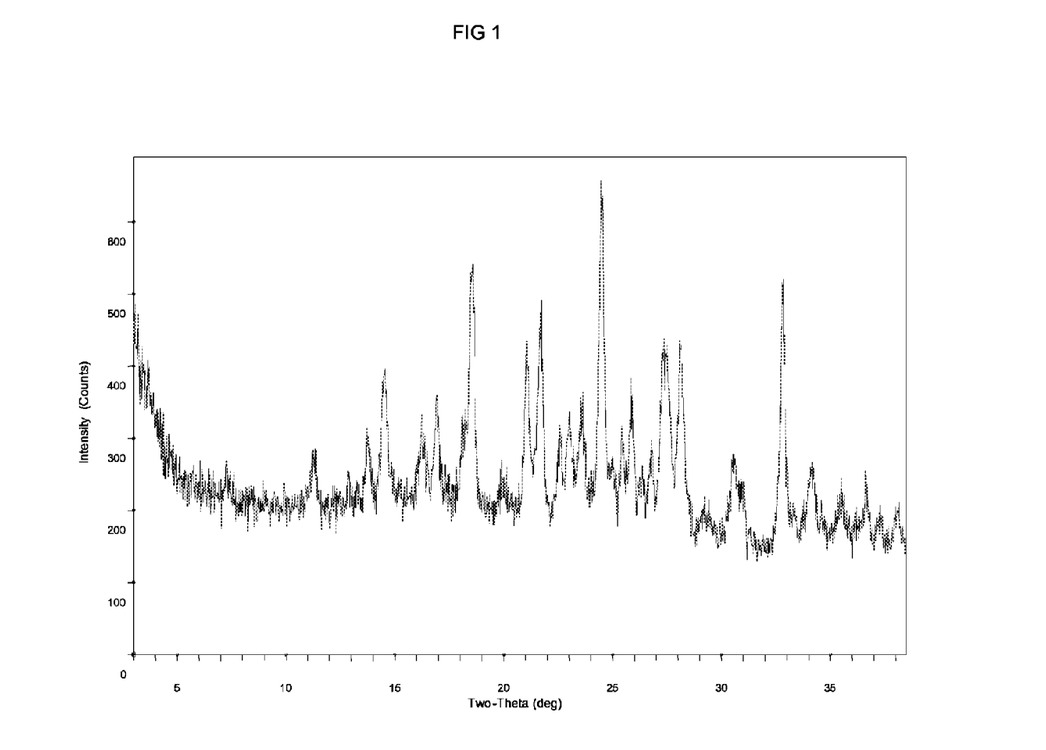
FIG. 1 depicts a Powder X-Ray Diffraction (PXRD) pattern of N-{(1S)-2-amino-1-[(3-fluorophenyl)methyl]ethyl}-5-chloro-4-(4-chloro-1-methyl-1H-pyrazol-5-yl)-2-thiophenecarboxamide in crystalline form.

Preparation of: Crystalline N-{(1S)-2-Amino-1-[(3-fluorophenyl)methyl]ethyl}-5-chloro-4-(4-chloro-1-methyl-1H-pyrazol-5-yl)-2-thiophenecarboxamide hydrochloride Amorphous N-{(1S)-2-amino-1-[(3-fluorophenyl)methyl]ethyl}-5-chloro-4-(4-chloro-1-methyl-1H-pyrazol-5-yl)-2-thiophenecarboxamide free base is prepared as described in International Application No. PCT/US08/053269. 1 mL of methyl t-butyl ether (MTBE) is added to a vial containing 50.8 mg of amorphous N-{(1S)-2-amino-1-[(3-fluorophenyl)methyl]ethyl}-5-chloro-4-(4-chloro-1-methyl-1H-pyrazol-5-yl)-2-thiophenecarboxamide free base. Most of the solid dissolved. After addition of the HCl acid (1 eq., 29.7 mL of 4M HCl in 1,4-dioxane) to the reaction mixture, a white solid material crashed out quickly at room temperature. An aliquot of the reaction mixture was analyzed by polarized light microscopy (PLM) and the solid was found to be amorphous. The slurry was then heated to 40° C. with magnetic stirring to dissolve most of the solid material. The thin slurry was stirred at 40° C. overnight, and then cooled from 40° C. to 25° C. A thick white slurry formed. An aliquot of the reaction mixture was analyzed by polarized light microscopy (PLM) and the solid was found to be crystalline. The white solid was collected by vacuum filtration, and then dried at 50° C. overnight. The product was determined be a crystalline solid by the Powder X-Ray Diffraction (PXRD) pattern depicted in FIG. 1.
Instrument: Rigaku Miniflex II, Serial DD02652
Key Operating Parameters:
Method Normal Run
The sample is scanned using the following parameters:
Scan range: 2-40 degrees two-theta
Generator power: 30 kV, 15 mA
Radiation Source: Cu KAlpha
Scan mode: FT
Count time: 1.0 seconds
Step width: 0.020 degrees two-theta per step
Scan axis: 2 theta/theta
Incident Beam optics: ±2.5° divergence angle soller slit, 1.25 degree divergent slit, 0.3 mm
RecSlit, 1.25 degrees anti-scatter slit
Diffracted Beam optics: fixed slits (MiniFlex II), ±2.5° soller slits
Detector Type Rigaku MiniFlex II SC (Scintillator Counter)
The sample is packed into a zero background sample holder (100 μm indent) and gently flattened using a glass slide.

EXAMPLE 2

Figure 2:
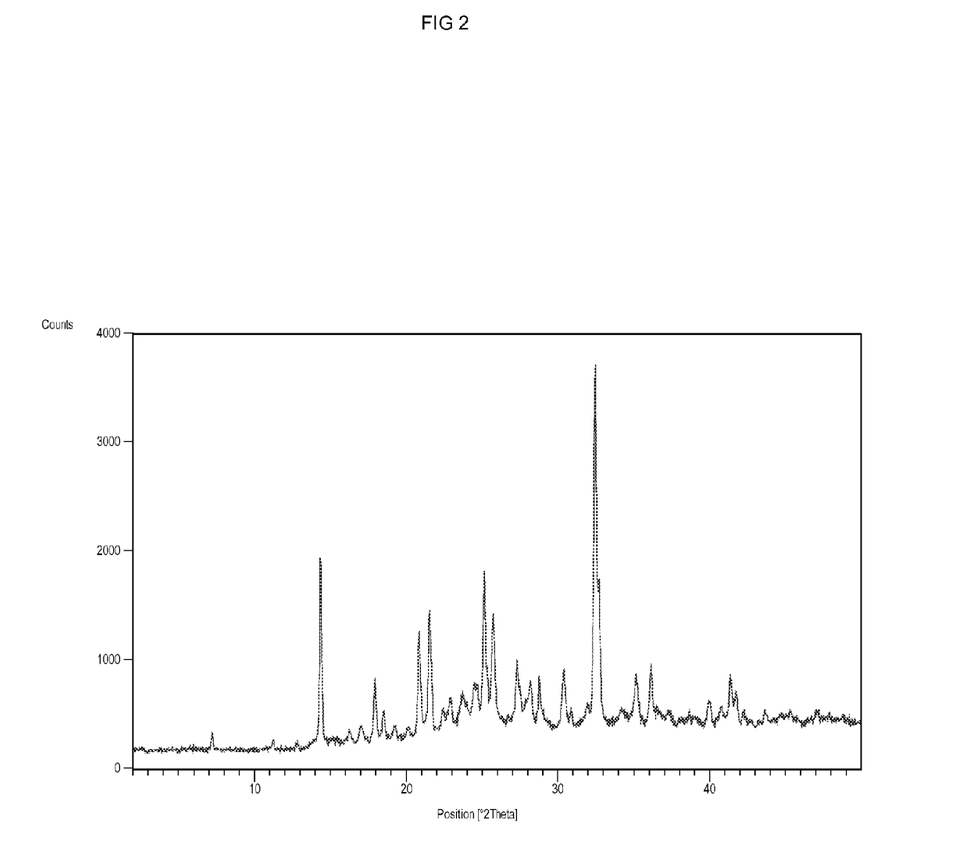
FIG. 2 depicts a Powder X-Ray Diffraction (PXRD) pattern of N-{(1S)-2-amino-1-[(3-fluorophenyl)methyl]ethyl}-5-chloro-4-(4-chloro-1-methyl-1H-pyrazol-5-yl)-2-thiophenecarboxamide in crystalline form.

Preparation of: Crystalline N-{(1S)-2-Amino-1-[(3-fluorophenyl)methyl]ethyl}-5-chloro-4-(4-chloro-1-methyl-1H-pyrazol-5-yl)-2-thiophenecarboxamide hydrochloride 5 mL of MTBE was added to 213.9 mg of N-{(1S)-2-amino-1-[(3-fluorophenyl)methyl]ethyl}-5-chloro-4-(4-chloro-1-methyl-1H-pyrazol-5-yl)-2-thiophenecarboxamide amorphous free-base (0.500 mMol.). The mixture was heated to 40° C. with magnetic stirring for 1 hour. A solution of 4M HCl in 1,4-dioxane (1 eq; 125.1 uL) was added in four equal portions. After addition of the first portion (0.25 eq), the mixture was heated to 42° C. and 1 mL of acetonitrile was added to dissolve all of the solid material. After the remainder of the HCl solution was added, some solid material appeared. The slurry was stirred at 42° C. for 4 hours, then was cooled slowly to 22° C. overnight with 90 minute holds at 35° C., 30° C., and 25° C. The white solid material was filtered and dried at 50° C. under vacuum with a slow nitrogen bleed overnight. The yield was 73.6% (0.3685 mmol; 170.90 mg) of the HCl salt. The solid was found to be 1:1 stoichiometric HCl salt by ion chromatography, and to be crystalline by the Powder X-Ray Diffraction (PXRD) pattern depicted in FIG. 2 and as characterized by diffraction peaks below, and to have a melting point of 211° C.
PXRD Peaks (Values Given in Degrees Two-Theta with d-Spacing in Parenthesis):

| 7.2(12.20) | 14.4(6.16) | 17.9(4.94) | 18.5(4.79) | 20.8(4.26) |
| 21.5(4.12) | 22.4(3.96) | 22.9(3.88) | 23.7(3.75) | 24.5(3.63) |
| 24.7(3.61) | 25.1(4.12) | 25.7(3.46) | 27.3(3.26) | 28.2(3.16) |
| 28.8(3.10) | 30.4(2.94) | 32.4(2.76) | 32.7(2.73) | 35.2(2.55) |
| 36.1(2.48) | 40.0(2.25) | 41.3(2.18) | 41.7(2.16) | |

Instrument: PANalytical X'Pert-Pro MPD with Johansson Kα1 monochromator, using X'Celerator detector
Key Operating Parameters:
Radiation: Cu (Kα1), 1.540598 angstroms (monochromatic)
Detector: X'Celerator
Tension: 45 kV
Current: 40 mA
Start angle: 2.0° 2θ
End angle: 52.0° 2θ
Step size: 0.02°
Time/step: 40.0 sec
Scan speed: 0.05°/sec
Incident beam: 2° fixed anti-scatter slit, and programmable divergence slit
Diffracted beam: 0.02 rad soller slit, and programmable anti-scatter slit
Samples prepared on silicon zero background sample holder.

EXAMPLE 3

Figure 3:
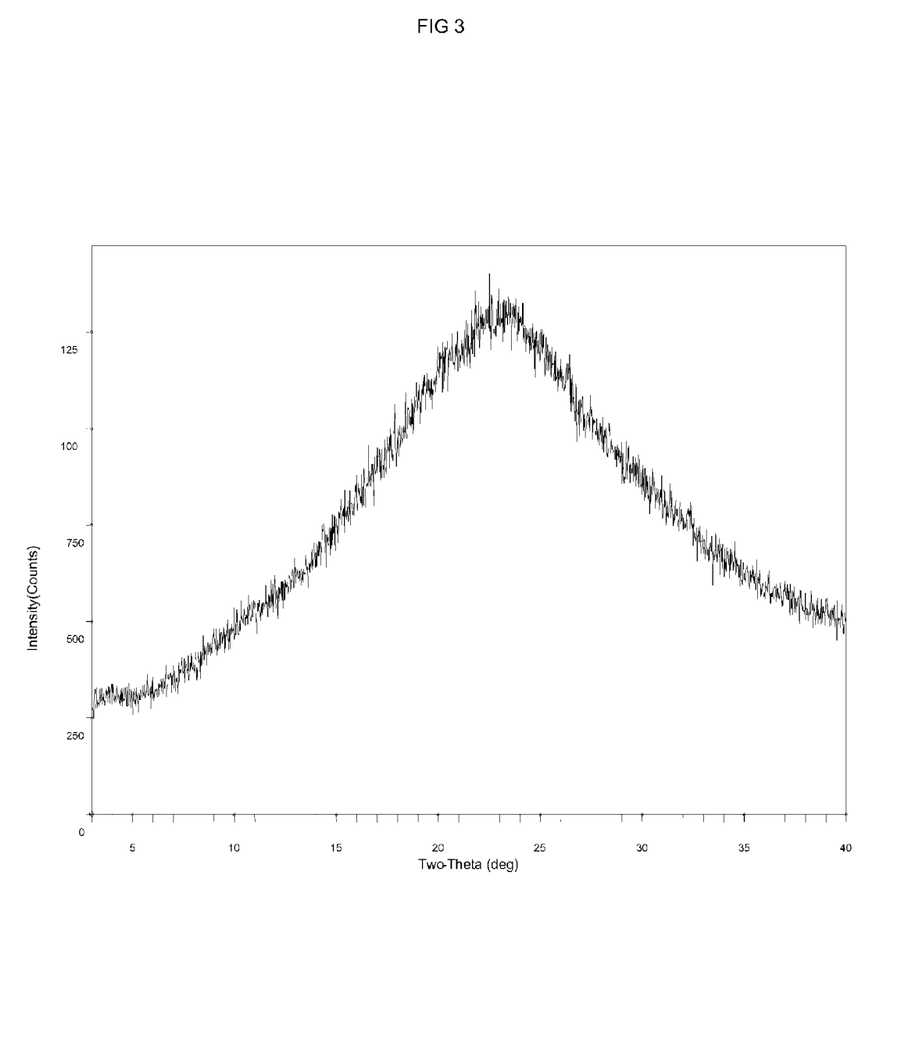
FIG. 3 depicts a Powder X-Ray Diffraction (PXRD) pattern of N-{(1S)-2-amino-1-[(3-fluorophenyl)methyl]ethyl}-5-chloro-4-(4-chloro-1-methyl-1H-pyrazol-5-yl)-2-thiophenecarboxamide in amorphous form.

Preparation of: Amorphous N-{(1S)-2-Amino-1-[(3-fluorophenyl)methyl]ethyl}-5-chloro-4-(4-chloro-1-methyl-1H-pyrazol-5-yl)-2-thiophenecarboxamide hydrochloride The hydrochloride salt of N-{(1S)-2-amino-1-[(3-fluorophenyl)methyl]ethyl}-5-chloro-4-(4-chloro-1-methyl-1H-pyrazol-5-yl)-2-thiophenecarboxamide prepared generally as described in Example 96 of International Application No. PCT/US2008/053269, having an International Filing date of Feb. 7, 2008, and having International Publication Number WO/2008/098104 and an International Publication Date of Aug. 14, 2008, which generally states that the free base compound, N-{(1S)-2-amino-1-[(3-fluorophenyl)methyl]ethyl}-5-chloro-4-(4-chloro-1-methyl-1H-pyrazol-5-yl)-2-thiophenecarboxamide, is treated with 4M HCl in dioxane and after 5 min, the solution is concentrated and dried under vacuum to afford N-{(1S)-2-amino-1-[(3-fluorophenyl)methyl]ethyl}-5-chloro-4-(4-chloro-1-methyl-1H-pyrazol-5-yl)-2-thiophenecarboxamide hydrochloride, yielded an amorphous solid as indicated by the Powder X-Ray Diffraction (PXRD) pattern depicted in FIG. 3.
Instrument: Rigaku Miniflex II, Serial DD02652
Key Operating Parameters:
Method Normal Run
The sample is scanned using the following parameters:
Scan range: 2-40 degrees two-theta
Generator power: 30 kV, 15 mA
Radiation Source Cu KAlpha
Scan mode: FT
Count time: 1.0 seconds
Step width: 0.020 degrees two-theta per step
Scan axis: 2 theta/theta
Incident Beam optics: ±2.5° divergence angle soller slit, 1.25 degree divergent slit, 0.3 mm RecSlit, 1.25 degrees anti-scatter slit
Diffracted Beam optics: fixed slits (MiniFlex II), ±2.5° soller slits
Detector Type Rigaku MiniFlex II SC (Scintillator Counter)
The sample is packed into a glass sample holder and gently flattened using a glass slide.

EXAMPLE 4

Tablet Composition

Lactose, microcrystalline cellulose, sodium starch glycolate, magnesium stearate and crystalline N-{(1S)-2-amino-1-[(3-fluorophenyl)methyl]ethyl}-5-chloro-4-(4-chloro-1-methyl-1H-pyrazol-5-yl)-2-thiophenecarboxamide hydrochloride are blended in the proportions shown in Table 1 below. The blend is then compressed into tablets.

TABLE 1

| INGREDIENT | mg. |
| --- | --- |
| crystalline N-{(1S)-2-amino-1-[(3-fluorophenyl)methyl]ethyl}-5-chloro-4-(4-chloro-1-methyl-1H-pyrazol-5-yl)-2-thiophenecarboxamide hydrochloride | 8.45 |
| microcrystalline cellulose | 112 |
| lactose | 70 |
| sodium starch glycolate | 8 |
| magnesium stearate | 2 |

EXAMPLE 5

Injectable Parenteral Composition

An injectable form for administering the active ingredient is produced by stirring 5.0 mg. of crystalline N-{(1S)-2-amino-1-[(3-fluorophenyl)methyl]ethyl}-5-chloro-4-(4-chloro-1-methyl-1H-pyrazol-5-yl)-2-thiophenecarboxamide hydrochloride in 1.0 ml. of normal saline.

EXAMPLE 6

Hygroscopicity

Crystalline

Crystalline N-{(1S)-2-amino-1-[(3-fluorophenyl)methyl]ethyl}-5-chloro-4-(4-chloro-1-methyl-1H-pyrazol-5-yl)-2-thiophenecarboxamide hydrochloride made generally according to Example 1, and confirmed to be crystalline by PXRD, was tested using a VTI instrument SGA 100 using the following method.

| Sample Preparation: | |
| --- | --- |
| Solvent: | Water |
| Drying Temp (° C.): | No drying |
| Experiment Temp (° C.): | 25 |
| Max Equilibrium Time (min) | 240 |
| Equilibrium Criteria (wt %): | 0.0025 in 10 min |
| Data Logging Interval (min): | 2 or 0.01 wt % |

There were 24 Relative Humidity steps used. The Relative Humidity at each step is as follows.

1-40; 2-50; 3-60; 4-70; 5-80; 6-90; 7-80; 8-70; 9-60; 10-50; 11-40; 12-30; 13-20; 14-10; 15-5; 16-10; 17-20; 18-30; 19-40; 20-50; 21-60; 22-70; 23-80; and 24-90.

The weight increase of the compound was less than 1% w/w moisture, indicating the compound has a low level of hygroscopicity.

Amorphous

In a separate experiment on a different day, amorphous N-{(1S)-2-amino-1-[(3-fluorophenyl)methyl]ethyl}-5-chloro-4-(4-chloro-1-methyl-1H-pyrazol-5-yl)-2-thiophenecarboxamide hydrochloride (confirmed to be amorphous by PXRD), was tested using a VTI instrument SGA 100 using the following method.

| Sample Preparation: | | | |
| --- | --- | --- | --- |
| Solvent: | Water | | |
| Drying Temp (° C.): | 60 | | |
| Heating Rate (° C./min): | 1 | | |
| Max Drying Time (min): | 120 | | |
| Experiment Temp (° C.): | 25 | | |
| Max Equilibrium Time (min) | 300 | | |
| Equilibrium Criteria (wt %): | 0.0025 | in | 10 min |
| Data Logging Interval (min): | 2 | or | 0.01 wt % |

There were 19 Relative Humidity steps used. The Relative Humidity at each step is as follows.

1-0; 2-10; 3-20; 4-30; 5-40; 6-50; 7-60; 8-70; 9-80; 10-90; 11-80; 12-70; 13-60; 14-50; 15-40; 16-30; 17-20; 18-10; and 19-0.

The weight increase of the compound was more than 18% w/w moisture, indicating the compound has a high level of hygroscopicity.

While the preferred embodiments of the invention are illustrated by the above, it is to be understood that the invention is not limited to the precise instructions herein disclosed and that the right to all modifications coming within the scope of the following claims is reserved.

What is claimed is:

1. The compound N-{(1S)-2-amino-1-[(3-fluorophenyl)methyl]ethyl}-5-chloro-4-(4-chloro-1-methyl-1H-pyrazol-5-yl)-2-thiophenecarboxamide hydrochloride in crystalline form, made by a process comprising the steps of:
   a) adding N-{(1S)-2-amino-1-[(3-fluorophenyl)methyl]ethyl}-5-chloro-4-(4-chloro-1-methyl-1H-pyrazol-5-yl)-2-thiophenecarboxamide and methyl t-butyl ether to form a mixture;
   b) adding HCl acid to the mixture and stir at above room temperature;
   c) allowing the mixture to return to room temperature; and
   d) isolate and dry the prepared compound.

2. A pharmaceutical composition comprising a compound of claim 1 and a pharmaceutically acceptable carrier or diluent.

3. A process for preparing a pharmaceutical composition containing a pharmaceutically acceptable carrier and an effective amount of a compound of claim 1, which process comprises bringing the compound of claim 1 into association with a pharmaceutically acceptable carrier.

4. A method of inhibiting Akt activity in a mammal, which comprises administering to such mammal an inhibitory amount of a compound of claim 1.

5. The method of claim 4 wherein the mammal is a human.

6. Crystalline N-{(1S)-2-amino-1-[(3-fluorophenyl)methyl]ethyl}-5-chloro-4-(4-chloro-1-methyl-1H-pyrazol-5-yl)-2-thiophenecarboxamide hydrochloride having characteristic diffraction peaks at 14.4°±0.3° and 32.4°±0.3° in an Powder X-Ray Diffractogram using Cu Kα radiation.

7. Crystalline N-{(1S)-2-amino-1-[(3-fluorophenyl)methyl]ethyl}-5-chloro-4-(4-chloro-1-methyl-1H-pyrazol-5-yl)-2-thiophenecarboxamide hydrochloride having the characteristic diffraction peaks recited in claim 6 and having characteristic diffraction peaks at 25.1°±0.3° and 25.7°±0.3° in the Powder X-Ray Diffractogram using Cu Kα radiation.

8. Crystalline N-{(1S)-2-amino-1-[(3-fluorophenyl)methyl]ethyl}-5-chloro-4-(4-chloro-1-methyl-1H-pyrazol-5-yl)-2-thiophenecarboxamide hydrochloride having the characteristic diffraction peaks recited in claim 7 and having characteristic diffraction peaks at 21.5°±0.3° and 20.8°±0.3° in the Powder X-Ray Diffractogram using Cu Kα radiation.

9. A pharmaceutical composition comprising the compound of claim 6 and a pharmaceutically acceptable carrier or diluent.

10. A method of inhibiting Akt activity in a mammal, which comprises administering to such mammal an inhibitory amount of a compound of claim 6.

11. The method of claim 10 wherein the mammal is a human.

* * * * *